(12) United States Patent
Biedermann et al.

(10) Patent No.: US 8,277,494 B2
(45) Date of Patent: Oct. 2, 2012

(54) BONE ANCHORING DEVICE

(75) Inventors: Lutz Biedermann, VS-Villingen (DE); Wilfried Matthis, Weisweil (DE); Stefan Freudiger, Bremgarten (CH)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 942 days.

(21) Appl. No.: 12/175,431

(22) Filed: Jul. 17, 2008

(65) Prior Publication Data

US 2009/0138052 A1     May 28, 2009

Related U.S. Application Data

(60) Provisional application No. 60/951,128, filed on Jul. 20, 2007.

(30) Foreign Application Priority Data

Jul. 20, 2007  (EP) .................................... 07014318

(51) Int. Cl.
  *A61B 17/86*  (2006.01)
(52) U.S. Cl. ......................... 606/301; 606/264; 606/279
(58) Field of Classification Search ........... 606/264–274
  See application file for complete search history.

(56) References Cited

U.S. PATENT DOCUMENTS

| | | | |
|---|---|---|---|
| 5,360,431 A | | 11/1994 | Puno et al. |
| 5,496,321 A | * | 3/1996 | Puno et al. ..................... 606/305 |
| 6,117,137 A | | 9/2000 | Halm et al. |
| 6,224,596 B1 | * | 5/2001 | Jackson ........................ 606/264 |
| 6,224,598 B1 | | 5/2001 | Jackson |
| 6,478,797 B1 | | 11/2002 | Paul |
| 6,652,526 B1 | | 11/2003 | Arafiles |
| 6,783,527 B2 | | 8/2004 | Drewry et al. |
| 7,018,379 B2 | | 3/2006 | Drewry et al. |
| 2003/0220642 A1 | | 11/2003 | Freudiger |
| 2005/0096659 A1 | | 5/2005 | Freudiger |
| 2005/0187548 A1 | | 8/2005 | Butler et al. |

(Continued)

FOREIGN PATENT DOCUMENTS

DE    G 94 03 231.9    6/1994

(Continued)

OTHER PUBLICATIONS

European Search Report, dated Apr. 9, 2008, corresponding to EP 07014318; European Search Report mailed Apr. 21, 2008; Biedermann Motech GmbH (12 pp.).

(Continued)

*Primary Examiner* — Nicholas Woodall
(74) *Attorney, Agent, or Firm* — Christie, Parker & Hale, LLP (57) ABSTRACT

A bone anchoring device includes an anchoring element having a shank to be anchored in a bone or a vertebra, a rod for connecting at least two anchoring elements, the rod being made of an elastic material. The bone anchoring device further includes a receiving part being connected to the shank for receiving the rod, a seat for the rod being provided in the receiving part the seat having a rod contacting surface, and a locking device cooperating with the receiving part for fixation of the rod in the seat. The locking device includes a rod contacting surface, wherein the rod contacting surface of the seat and/or the rod contacting surface of the locking device includes an engagement structure for engaging the rod, the engagement structure having an asymmetric cross section.

17 Claims, 8 Drawing Sheets

U.S. PATENT DOCUMENTS

| | | |
|---|---|---|
| 2005/0240180 A1 | 10/2005 | Vienney et al. |
| 2006/0122599 A1 | 6/2006 | Drewry et al. |
| 2007/0093820 A1* | 4/2007 | Freudiger .................. 606/61 |
| 2008/0114404 A1 | 5/2008 | Matthis et al. |

FOREIGN PATENT DOCUMENTS

| | | |
|---|---|---|
| DE | 198 18 765 A1 | 10/1999 |
| DE | 298 10 798 U1 | 12/1999 |
| EP | 0 346 521 A1 | 12/1989 |
| EP | 1 527 742 A1 | 5/2005 |
| EP | 1759646 A1 | 3/2007 |
| EP | 1795134 A1 | 6/2007 |
| FR | 2 829 014 A1 | 3/2003 |
| WO | WO 95/14176 A1 | 5/1995 |

OTHER PUBLICATIONS

OA dated Nov. 27, 2009 for U.S. Appl. No. 11/854,508 (13 sheets).
OA dated May 21, 2010 for U.S. Appl. No. 11/854,508 (15 sheets).
OA dated Dec. 7, 2010 for U.S. Appl. No. 11/854,508 (16 sheets).
OA dated May 25, 2011 for U.S. Appl. No. 11/854,508 (3 sheets).
OA dated Jan. 17, 2012 for U.S. Appl. No. 11/854,508 (13 sheets).
OA dated Oct. 1, 2008 for U.S. Appl. No. 11/512,461 (8 sheets).
OAa dated May 22, 2009 for U.S. Appl. No. 11/512,461 (8 sheets).
OA dated Jan. 20, 2010 for U.S. Appl. No. 11/512,461 (9 sheets).
OA dated Aug. 2, 2010 for U.S. Appl. No. 11/512,461 (10 sheets).
OA dated Dec. 17, 2010 for U.S. Appl. No. 11/512,461 (2 sheets).
OA dated Jun. 21, 2011 for U.S. Appl. No. 11/512,461 (7 sheets).

* cited by examiner

PRIOR ART

BONE ANCHORING DEVICE

CROSS-REFERENCE TO RELATED APPLICATION(S)

This application claims the benefit of U.S. Provisional Application, Ser. No. 60/951,128, filed Jul. 20, 2007, the contents of which are hereby incorporated by reference in their entirety, and claims priority European Patent Application EP 07 014 318.5, filed Jul. 20, 2007, the contents of which are hereby incorporated by reference in their entirety.

BACKGROUND

The present application relates to a bone anchoring device for the dynamic stabilization of bones, in particular for the dynamic stabilization of the spine. The bone anchoring device includes a bone anchoring element which can be connected to a flexible rod being made of an elastic material. For fixation of the rod, an engagement structure is provided which has such a shape that the pressure distribution on the rod in the fixed state is equalized.

EP 1 759 646 A1 discloses a spinal implant for the dynamic stabilization of the spine which uses a flexible rod made of an elastomer material. The rod is fixed in the receiving part by means of a locking device which clamps the rod by frictional forces with indirect form-fit contribution.

EP 1 795 134 A1 discloses a polyaxial screw for use with a flexible rod made of an elastomer material. To fix the rod or hold the rod in place, an engagement structure is provided in the receiving part receiving the rod and on the locking device locking the rod in the receiving part. The engagement structure comprises ribs or grooves which have a symmetric cross section in each sectional plane. The ribs press onto the elastomer rod causing a depression in the surface of the rod, while leaving the surface structure of the rod intact.

In some circumstances, in particular if high tensional loads act onto the rod, it is necessary to apply a high clamping force on the rod via the locking device to fix the rod. In such a case, there might be the risk that local pressure peaks could result in a structural damage with increased abrasion of the surface of the rod caused by the engagement structure. To avoid this, the height of the engagement structure could be reduced.

Based on the above, there is a need for a bone anchoring device which provides a safe fixation of the rod under high load conditions, and in particular, under high tensional load conditions acting onto the rod

SUMMARY

According to aspects of the disclosure, a bone anchoring device is provided which has a bone anchoring element and a rod, the rod being made of an elastic material, which can be used under high load conditions, in particular under high tensional load conditions acting onto the rod, and which nevertheless provides a safe fixation of the rod.

The bone anchoring device according to aspects of the disclosure optimizes the load distribution on the rod caused by the engagement structure in such a way that pressure peaks acting onto the surface of the rod in certain areas are avoided and the pressure distribution is made more uniform. Therefore, the risk of an abrasion or violation of the surface of the rod which can cause a loosening of the fixation is avoided. With the bone anchoring device according to the disclosure it is possible to transfer a high axial force from the rod to the bone anchoring element without rupture of the rod and to generate as little abrasion as possible when repeatedly fixed and loosened, for example during secondary adjustments.

Further features and advantages of the disclosure will become apparent and will be best understood by reference to the following detailed description of embodiments taken in conjunction with the accompanying drawings.

DETAILED DESCRIPTION

As shown in FIGS. 1 to 5, a bone anchoring device according to a first embodiment includes a bone anchoring element 1 having a shank 2 with a bone thread and a tip at one end and a receiving part 3 at the opposite end. The receiving part 3 is substantially cylindrically shaped and includes a substantially U-shaped recess 4 forming two free legs 5,6. An internal thread 7 is provided on the legs. The bottom of the U-shaped recess forms a seat 8 for receiving a rod 9. The rod 9 is used to connect several bone anchoring elements. To secure the rod 9 in the recess 4, a locking device in the form of an inner screw 10 is provided which can be screwed-in between the legs 5,6.

The rod 9 is made of a biocompatible, elastic material, preferably of plastics. In particular, the material is a free-flowing material. For example, the rod 9 is made of an elastomer material including polycarbonate-polyurethane or polycarbonate urethane (PCU).

Figure 1:
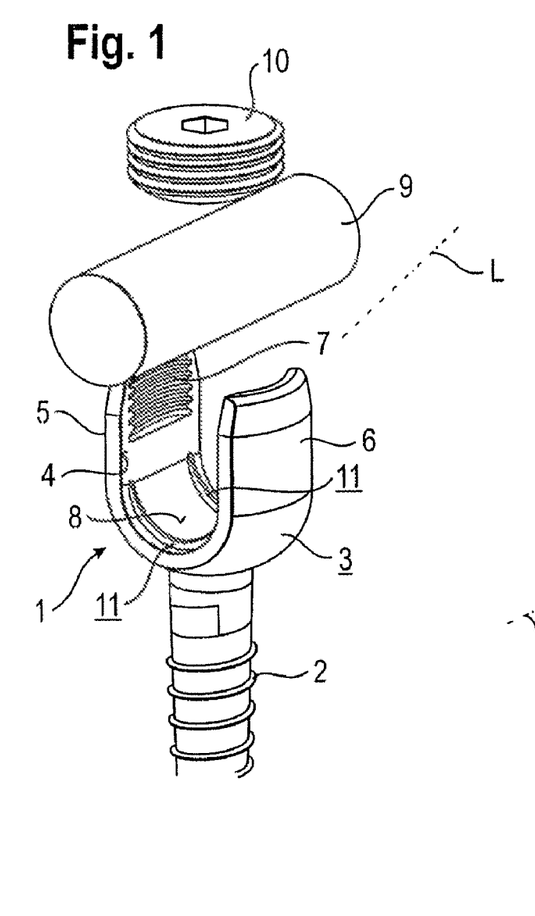
FIG. 1 shows an exploded perspective view of a bone anchoring device according to a first embodiment of the disclosure.
Figure 2:
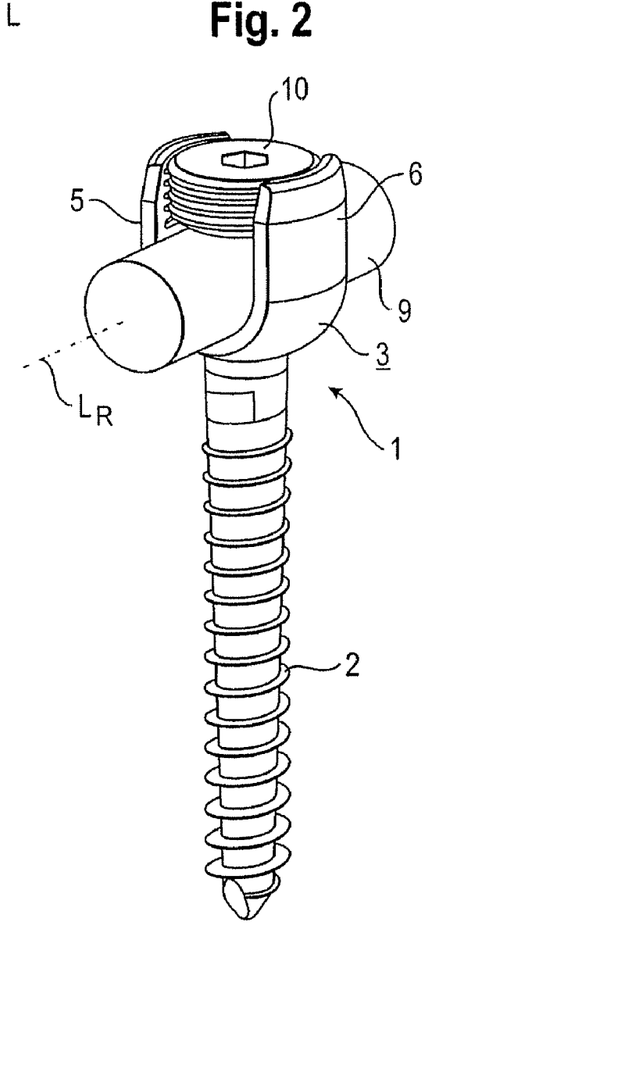
FIG. 2 shows the bone anchoring device of FIG. 1 in an assembled state.
Figure 4:
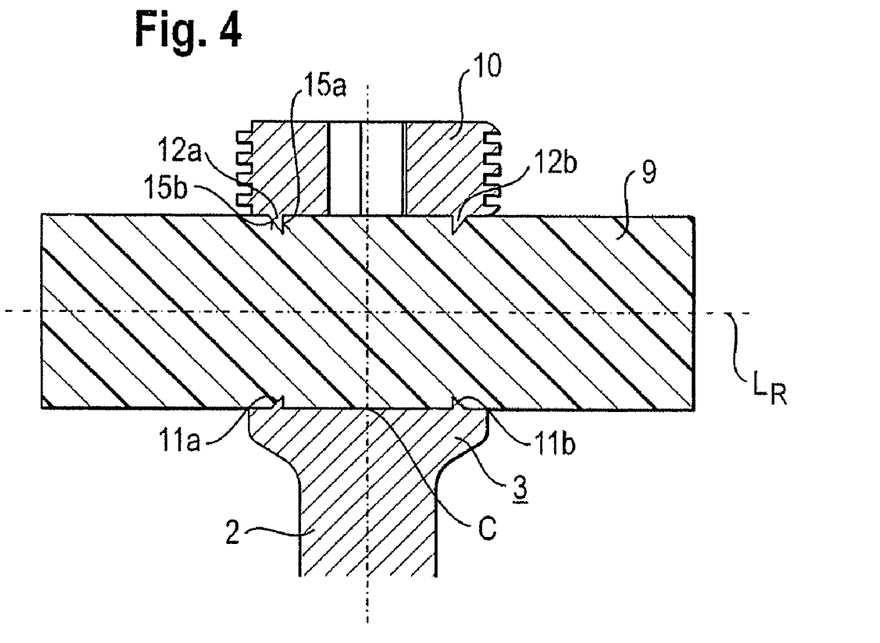
FIG. 4 shows a sectional view of the bone anchoring device according to FIG. 2 in a plane containing the rod axis.
Figure 5:
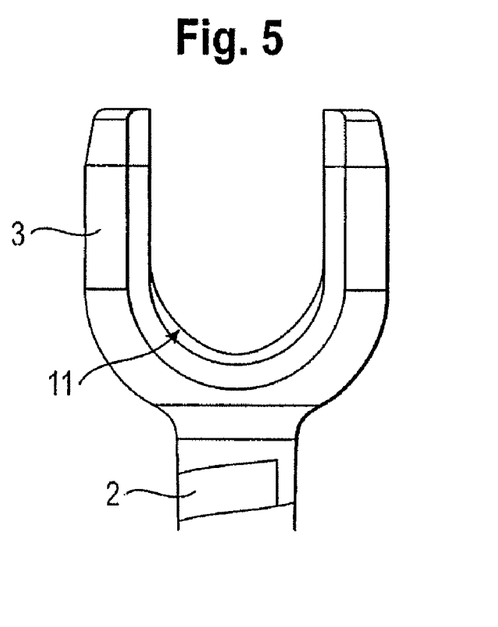
FIG. 5 shows a side view of the bone anchoring element of FIG. 1.

As can be seen in particular in FIGS. 1,4 and 5, rib-like projections 11 are provided on the surface of the seat 8. The rib-like projections 11 extend in a direction perpendicular to the longitudinal axis L of the recess 4. Therefore, the rib-like projections 11 extend perpendicular to the longitudinal axis $L_R$ of the rod 9. The rib-like projections 11 have such a length that they form a curvature corresponding to the seat 8. The rib-like projections 11 end at a distance from the internal thread 7. The rib-like projections 11 may run out on one or on either side in groove-like recesses which provide depressions in the surface of the seat 8 (not shown). Alternatively, depressions in the surface of the seat adjoining the rib-like projections can be provided to allow a material to flow into these depressions.

In the embodiment shown, the two rib-likes projections 11 are provided at a distance from the center of the seat 8 in the direction of the rod axis $L_R$. Preferably the distance from the outer ends of the seat 8 to the rib-like projection 11 is smaller than the distance between the rib-like projection 11 and the center of the seat 8. Accordingly, the rib-like projections 11 are provided in the outer region of the seat 8. To achieve secure clamping, two rib-like projections 11 on the seat are sufficient.

The inner screw 10 which is to be screwed in between the legs 5,6 includes at its lower side 10a which faces the rod 9 a ring-shaped projection 12 in the form of an annular rib with a central cavity. When, as shown in FIG. 4, the ring-shaped projection 12 comes into contact with the rod 9, two contact areas 12a, 12b are provided where the ring-shaped projection 12 presses onto the rod 9. The diameter of the ring-shaped projection 12 is such that the contact areas 12a,12b are located at the same position but at the opposite side of the surface of the rod 9 where the contact areas 11a and 11b of the rib-like projections 11 of the seat 8 are located.

Figure 6:
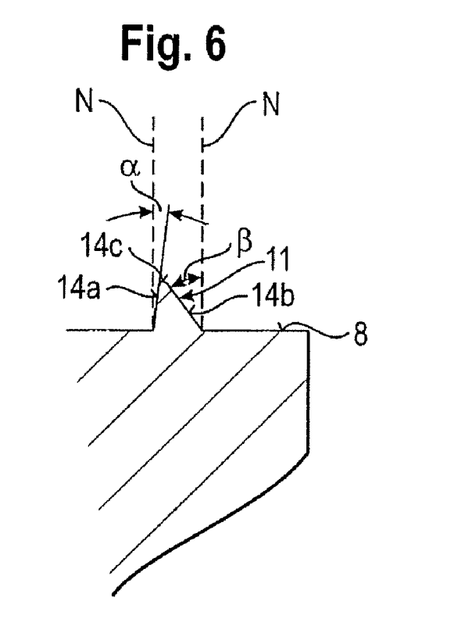
FIG. 6 shows an enlarged portion of containing the engagement structure of the bone anchoring element of FIG. 5.

As shown in particular in FIGS. 4 and 6, the rib-like projection 11 and the ring-shaped projection 12 have an asymmetric cross section in a plane containing the longitudinal axis $L_R$ of the rod 9 or in a plane parallel thereto. As shown in FIG. 6, the cross section is substantially triangle shaped resulting in a first flank 14a and an opposite second flank 14b which have a different inclination. In the embodiment shown, the first flank 14a includes an angle α with the normal N to the surface of the seat 8 which is approximately 100, and the second flank 14b includes an angle β with the normal N to the surface of the seat 8 which is approximately 35°. Other angles are also possible, as long as one flank is steeper than the other flank, i.e., α<β, for example, α<45° and α<β. The angle α is preferably between greater than 0° and smaller than approximately 15°. The angle β is preferably between approximately 30° and approximately 45°. As shown in FIG. 6, the edge 14c of the rib-like projection 11 is rounded. The second projection on the seat 8 which is shown in FIG. 1 has a similar structure except that the orientations of the first and second flank are mirrored. Accordingly, the steep flanks 14a are oriented towards the center C of the seat 8, as shown in FIG. 4.

Figure 3:
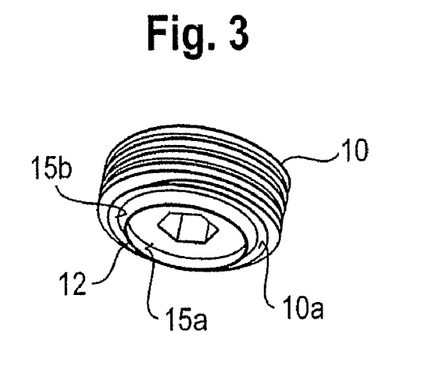
FIG. 3 shows a perspective view of the locking device of the bone anchoring device according to FIG. 1.

As shown in FIGS. 3 and 4 the ring-shaped projection 12 of the locking device also has an asymmetric cross section having a first flank 15a and a second flank 15b with different inclinations. The steep flank 15a is facing the center of the ring-shaped projection 12 and the flank 15b is directed outward. The angles α and β are preferably the same as those of the rib-like projections 11.

As can be seen in FIG. 4, the orientation of the flanks of the rib-like projection 11 and of the ring-shaped projection 12 are such that the steep flanks are directed towards the center of the seat and of the inner screw, respectively. As a consequence thereof, the outer flanks having the smaller inclination are directed to the outer areas of the anchoring element or the locking device, respectively.

The bone anchoring element 1 and the inner screw 10 are made of a biocompatible rigid material, preferably of a metal, such as titanium or a titanium alloy.

In use, first at least two bone anchoring elements are screwed into adjacent vertebrae, for example into the pedicles of the vertebrae. Thereafter, the rod 9 is inserted into the receiving parts 3 until it is seated in the seat 8. Then the rod 9 is locked in its position by screwing-in the inner screw 10. When the inner screw 10 is not yet tightened, the position of the rod 9 can still be adjusted in a stepless manner, since the rod 9 has a smooth surface. After adjusting the position of the rod 9, the inner screw 10 is tightened until the ring-shaped projection 12 comes into contact with the surface of the rod 9. As can be seen in FIG. 4, the opposite contact areas 12a and 12b of the ring-shaped projection 12 are pressed down into the surface of the rod 9. Similarly, the rib-like projections 11 are pressing on the surface of the rod 9 from below. The projections do not harm the integrity of the surface of the rod 9. The rod 9 begins to flow under applied pressure. This material flow results in an indirect form-fit connection. The combination of direct frictional forces and indirect form-fit forces holds the rod 9 in place.

Figure 7:
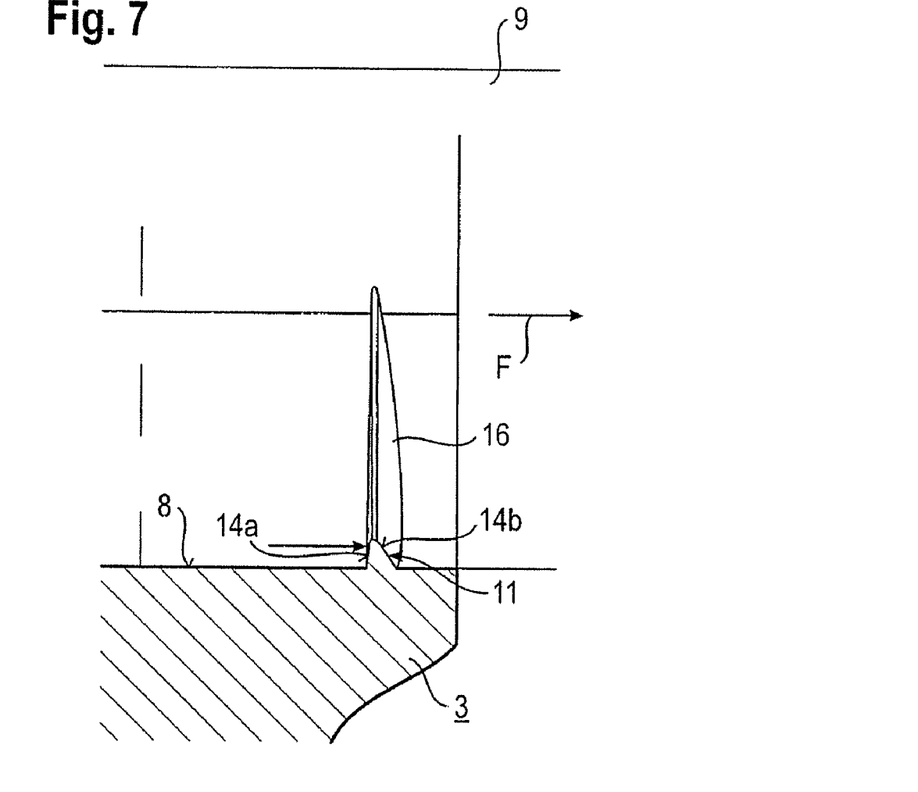
FIG. 7 shows partially sectional view of the bone anchoring device according to FIG. 4 without the locking element.

FIG. 7 shows a partial sectional view of a part of the receiving part 3 with seat 8 and rib-like projection 11 shown in section and the rod 9. A depression 16 is shown which is caused by pressure of the rib-like projection 11 pressing onto the rod 9. When the rod 9 is fixed and a force F acts in the longitudinal direction of the rod 9, the steep flank 14a provides the counterforce against translational movement of the rod 9. The counterforce provided by the steep flank 14a is larger than the counterforce which would be provided by a flank having the same inclination than the flank 14b at the same local pressure.

Figure 8:
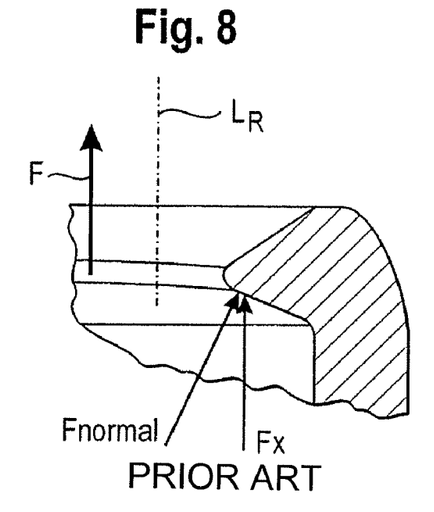
FIG. 8 shows a schematic view of the forces acting onto the rod in the conventional bone anchoring device.
Figure 9:
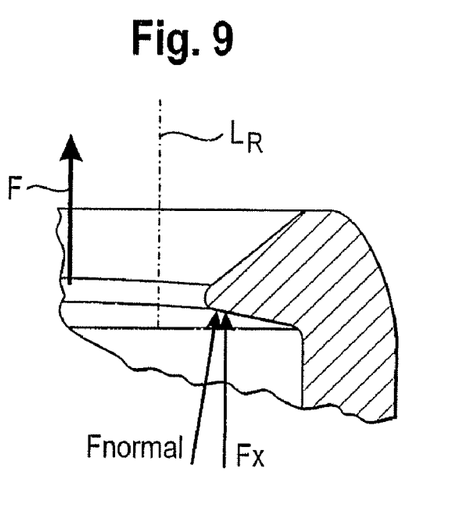
FIG. 9 shows a schematic sectional view of the forces acting onto the rod and the engagement structure in a bone anchoring device according to the first embodiment disclosure.

As can be seen in FIGS. 8 and 9, the normal force $F_{normal}$ of the force F acting in longitudinal direction of the rod 9 is larger in the conventional design of the rib which has symmetric shape (FIG. 8), compared to the normal force $F_{normal}$ for the asymmetric engagement structure (FIG. 9). In FIGS. 8 and 9, $F_x$ represents the component of force F in the longitudinal direction of the rod 9. Hence, to fix the rod with the symmetric rib-like projection 11 as shown in FIG. 8, a larger clamping force exerted by the locking device is necessary than in the case of the asymmetric rib-like projection 11 as shown in FIG. 9. Therefore, the local pressure applied to the rod via the engagement structure can be reduced with the asymmetric design of the engagement structure.

Preferably, only two rib-like projections 11 are provided in the seat as shown in FIG. 4, the distance of which corresponds to the diameter of the ring-shaped projection 12 on the lower surface of the inner screw 10. The orientation of the flanks is mirror-symmetrical, so that the effect described above can be obtained for tensional loads acting in one or the opposite longitudinal direction of the rod 9.

Figure 10A:
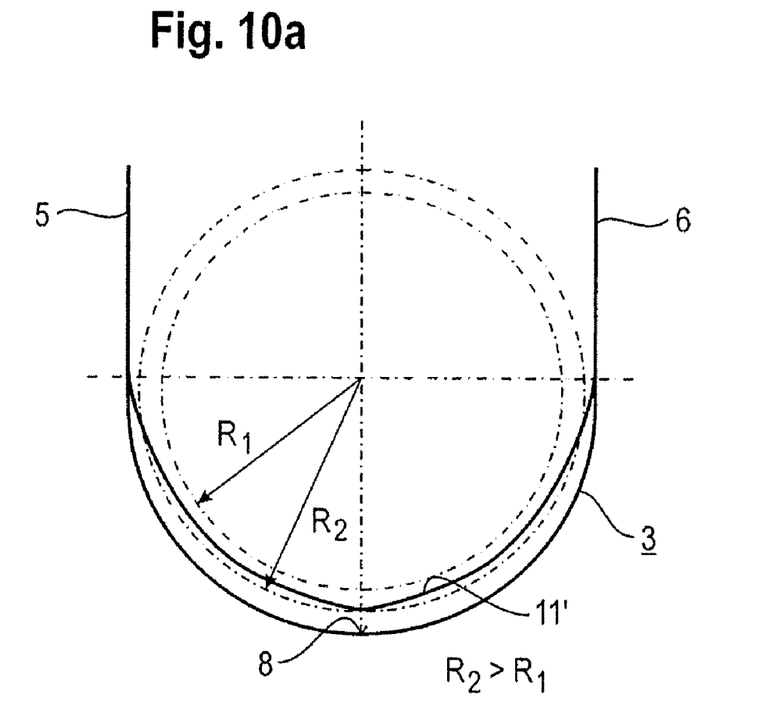
FIG. 10a schematically shows a second embodiment of the disclosure.

FIG. 10a shows a schematic view of the receiving part 3 of the bone anchoring device according to a second embodiment seen in the direction of the rod axis. The rib-like projection 11' in this embodiment is non-concentric about the rod axis $L_R$. The distance from the rod axis $L_R$ varies between a radius $R_1$ and $R_2$, wherein $R_2$ is greater than $R_1$. At the bottom of the seat 8 the height of the rib-like projection 11' is the smallest while the height of the projection 11' is increasing in a direction varying from the center of the seat and thereafter decreasing again when it runs out into the direction of the legs 5,6.

Figure 10B:
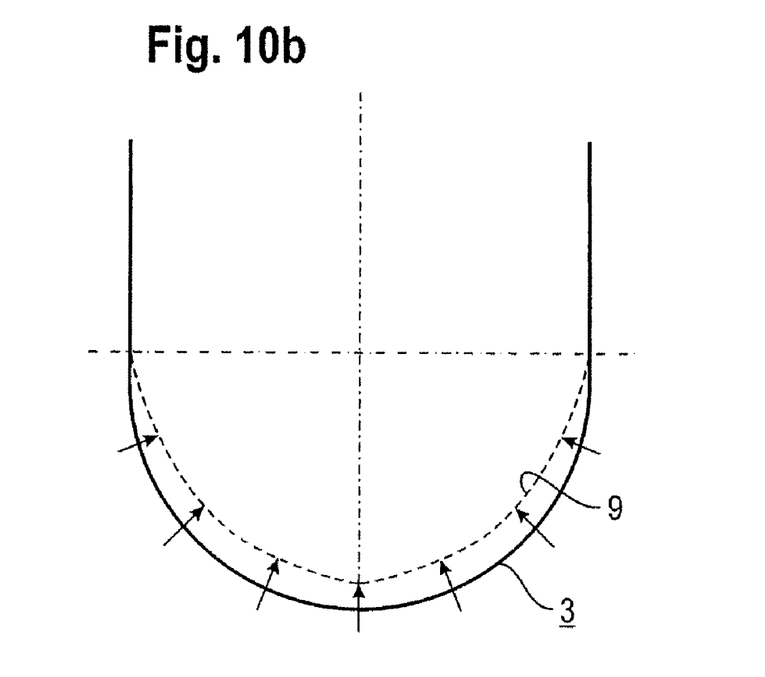
FIG. 10b shows a schematic view of the pressure distribution acting onto the rod according to the second embodiment.
Figure 11:
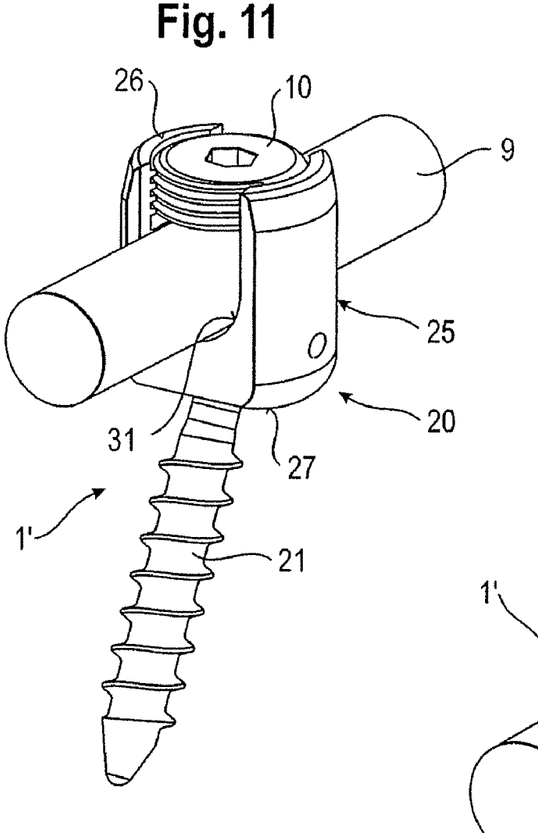
FIG. 11 shows a perspective view of the bone anchoring device according to a third embodiment in an assembled state.
Figure 12:
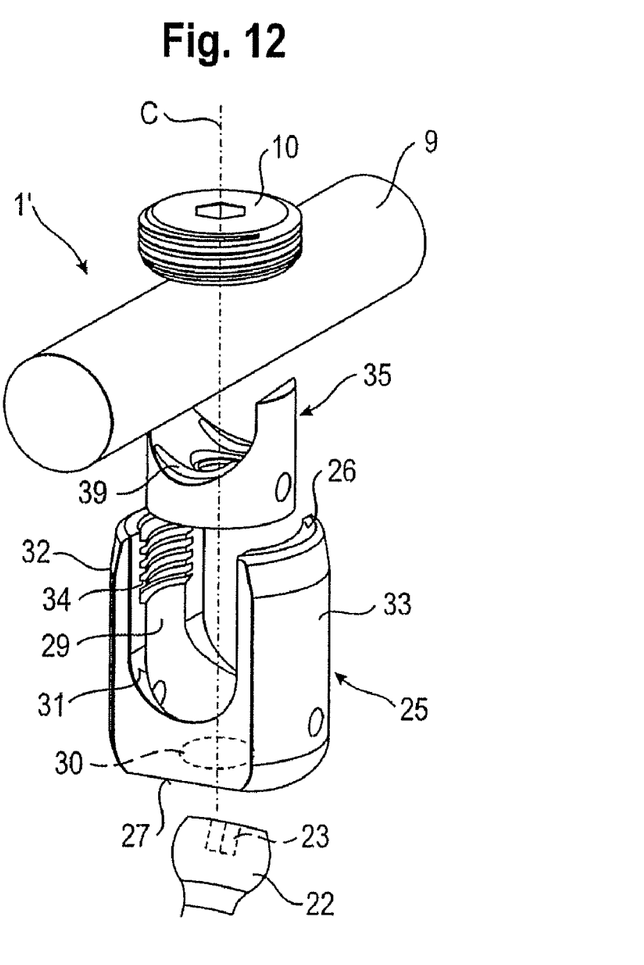
FIG. 12 shows an exploded view of the bone anchoring device according to FIG. 11.
Figure 13:
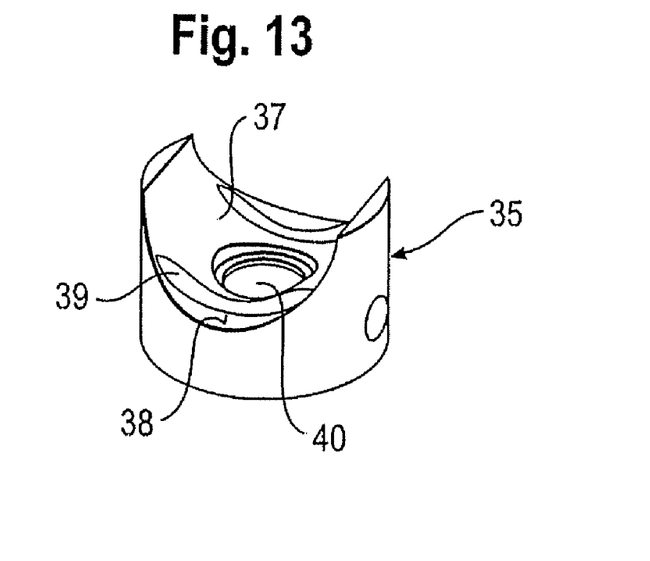
FIG. 13 shows a perspective view of the pressure element of the bone anchoring device according to FIG. 12.
Figure 14:
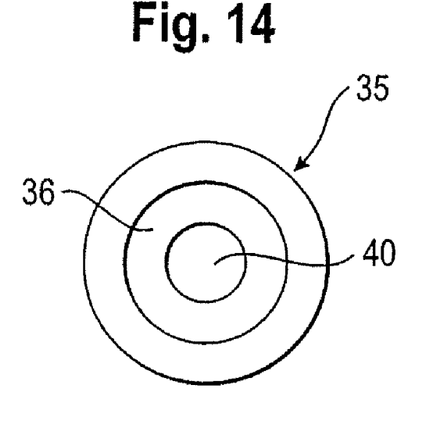
FIG. 14 shows a bottom view of the pressure element of FIG. 13.
Figure 15:
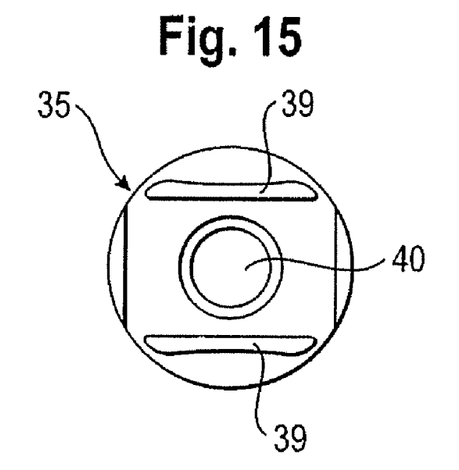
FIG. 15 shows a top view of the pressure element of FIG. 13.
Figures 16, 17:
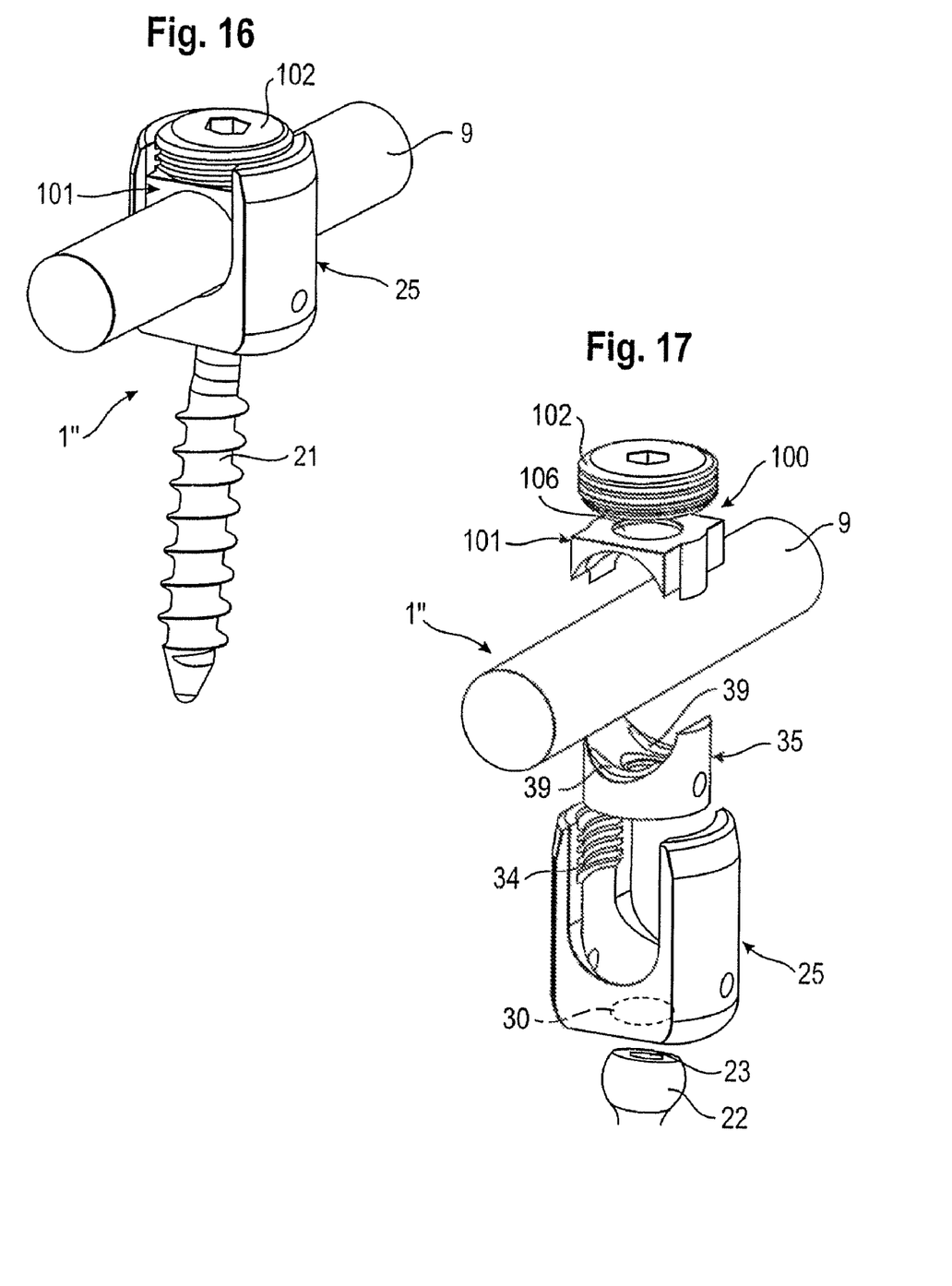
FIG. 16 shows a perspective view of a bone anchoring device according to a fourth embodiment in an assembled state.
FIG. 17 shows an exploded view of the bone anchoring device of FIG. 16.
Figure 18:
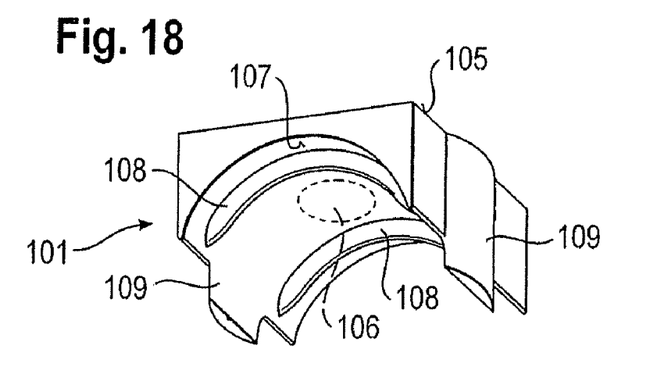
FIG. 18 shows a perspective view from the lower side of the filling piece of the bone anchoring device according to FIG. 17.
Figure 19:
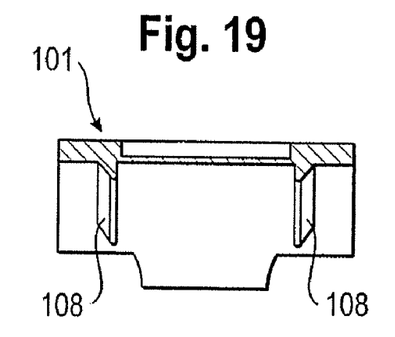
FIG. 19 shows a sectional view of the filling piece of FIG. 18.
Figure 20:
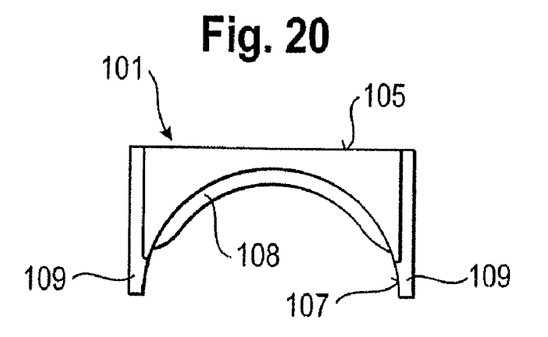
FIG. 20 shows a side view of the filling piece of FIG. 18.
Figure 21:
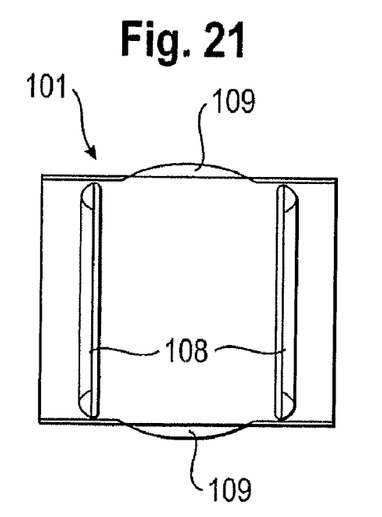
FIG. 21 shows a bottom view of the filling piece according to FIG. 18.
Figure 22:
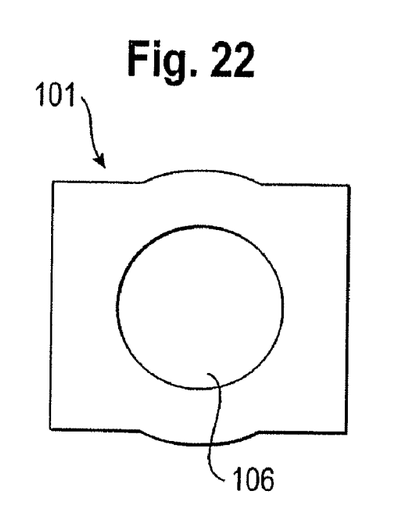
FIG. 22 shows a top view of the filling piece according to FIG. 18.

As can be seen in FIG. 10b this results in a more uniform pressure distribution acting onto the rod 9. Uniform pressure distribution means that there are no local pressure peaks. In this embodiment, the cross section of rib-like projection 11' can be symmetric or asymmetric in a plane containing the longitudinal axis of the rod $L_R$.

FIGS. 11 to 15 show a third embodiment of the disclosure in the form of a polyaxial bone anchoring device. The bone anchoring device 1' includes a bone anchoring element 20 in the form of a polyaxial bone screw having a screw element with a shank 21 with a bone thread, a tip at one end and a spherical head 22 at the opposite end. A recess 23 for engagement with the screwing-in tool is provided at the side of the head 22 which is opposite to the shank.

The bone anchoring element 20 further includes a receiving part 25 which has a first end 26 and a second end 27 opposite to the first end and a central axis C intersecting the plane of the first end and the second end. Coaxially with the central axis C a bore 29 is provided which extends from the first end to a distance from the second end. At the second end 27 an opening 30 (shown in dashed line) is provided the diameter of which is smaller than the diameter of the bore 29. The head 22 is pivotably held in the receiving part 25 with the shank extending through the opening 30.

The receiving part 25 further has a substantially U-shaped recess 31 which starts at the first end 26 and extends in the direction of the second end 27. By means of the U-shaped recess two free legs 32,33 are formed, which have an internal thread 34.

A pressure element 35 is provided which has a substantially cylindrical construction with an outer diameter which is only slightly smaller than the inner diameter of the bore 29 to allow the pressure element 35 to be introduced into the bore 29 of the receiving part and to be moved in the axial direction. On its lower side facing towards the second end 27, the pressure element 35 includes a spherical recess 36 the radius of which corresponds to the radius of the spherical head 22 of the screw element. On the opposite side the pressure element 35 includes a U-shaped recess 37 extending transversely to the central axis C. The lateral diameter of this recess is selected such that the rod 9 which is to be received in the receiving part 25 can be inserted into the recess 37 and guided laterally therein. The depth of the U-shaped recess 37 is such that in an assembled state when the rod is placed into the U-shaped recess 37, the pressure element 35 does not project over the upper surface of the rod 9.

The bottom of the U-shaped recess 37 of the pressure element 35 forms a seat 38 for the rod 9. Similar to the first embodiment two rib-like projections 39 are provided on the surface of the seat 38. The rib-like projections 39 extend in a direction transversely to the longitudinal axis of the U-shaped recess 37 and, therefore, transversely to the longitudinal axis $L_R$ of the rod 9. As can be seen in particular in FIG. 15, the rib-like projections 39 have an asymmetric shape with a steep flank directed to the center of the pressure element 35. The pressure element further includes a coaxial bore 40 to allow access to the recess 23 of the head 22 with a screwing-in tool.

The locking device is the inner screw 10 as in the first embodiment which has the ring-shaped projection 12 on its side 10a facing the rod 9. The dimensions of the ring-shaped projection 12 are such that the projection contacts the surface of the rod 9 at the opposite side of the rib-like projections 39, respectively.

In use, the bone anchoring device 1' can be preassembled, i.e. the bone screw is pivotably held in the receiving part and the pressure element is inserted and slightly held in a position in which its U-shaped recess is aligned with the U-shaped recess of the receiving part. The bone anchoring element is screwed into the bone and the angular position of the receiving part relative to the bone screw is adjusted. The rod 9 is inserted and the inner screw 10 tightened until it clamps the rod. The function of the clamping is the same as in the first embodiment. When the inner screw is tightened, it presses onto the upper surface of the rod and hence presses down the pressure element onto the head 22 to lock the angular position of the head in the receiving part.

As the locking of the rod is achieved by pressing the projections 39, 12 into the surface of the rod 9 without harming the integral structure of the rod 9, a reversal of the locking and secondary adjustments are possible.

FIGS. 16 to 22 show a fourth embodiment of the bone anchoring device. The bone anchoring device 1" is of the polyaxial type as the third embodiment. Parts which are identical to the third embodiment are indicated with the same reference numerals and the description thereof is not repeated. The fourth embodiment differs from the third embodiment by the locking device. The locking device 100 is a two-part locking device and includes a filling piece 101 and an inner screw 102. The filling piece 101 is shown in detail in FIGS. 18 to 22. The filling piece 101 has a substantially square shaped upper end 105 with a circular opening 106 and a cylindrical recess 107 the radius of which corresponds to the radius of the rod 9. On the surface of the cylindrical recess 107, two rib-like projections 108 are provided which extend in a direction transverse to the axis of the cylinderical recess 107. The rib-like projections 108 each are shaped asymmetrically with a first steep flank facing the center of the filling piece and a second flank directed outwardly of the filling piece, respectively. The distance between the rib-like projections 108 corresponds to the distance of the rib-like projections 39 of the pressure element 35. In an assembled state, the rib-like projections of the pressure element 35 and the filling piece 101 are located on opposite sides of the surface of the rod 9, respectively.

The filling piece 101 further includes two projections 109 which fit into the space enclosed by the internal thread 34 to slide along the internal thread when the filling piece is inserted.

The dimension of the filling piece 101 and the pressure element 35 is such that the projections 109 come into contact with the upper end of the pressure element when the filling piece 101 is pressed onto the rod.

The inner screw 102 includes a cylindrical projection (not shown) fitting into the opening 106 of the filling piece in such a way that it can still rotate therein.

In use, the bone anchoring element and the receiving part and a pressure element can be preassembled. The bone anchoring element is screwed into the bone. Then, the rod 9 is inserted and the locking device comprising the filling piece 101 and the inner screw 102 is inserted. The inner screw is tightened thereby pressing the filling piece 101 onto the surface of the rod. Hence, the rod is clamped between the pressure element and the filling piece and the engagement structure in form of the ribs 39 and the ribs 108 engages the surface of the rod as in the previous embodiments. By pressing down the filling piece, the pressure element is also pressed down and locks the head 22 in its rotational position.

Modifications of the above described embodiments are possible. Features of one embodiment can be combined with that of another embodiment.

The number of the rib-like projections can vary. Also, a combination of projections and depressions can be provided. In this case, it is of advantage that also the depressions have an asymmetric cross section. This allows the material which is displaced when the projections press onto the surface of the rod to flow out of the depressions to generate an indirect form-fit connection. The depressions can have a symmetric or asymmetric cross section. If the depressions also have an asymmetric cross section the clamping force of the rod can be reduced further while maintaining the same axial reaction loads.

The rod needs not to have a circular cross section, it can have an oval, rectangular, square or triangular cross section as well.

The projections and/or depressions need not to have a rib or groove-like structure, but can have any shape, as long as at least the projections have an asymmetric cross section having at least two flanks, one of which is steeper than the other.

The receiving part and the pressure element can be modified in many known ways. For example, the receiving part can be designed such that the head 22 of the bone anchoring element can be introduced from the bottom. The pressure element can extend above the surface of the rod when the rod is inserted and the locking device 10 can be a two-part locking device including inner set screw and an outer screw in the known manner. In this case, the inner set screw has the engagement structure. The locking devices also can be an outer nut or can include an outer nut cooperating with the legs of the receiving part.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring device comprising:
   an anchoring element having a shank to be anchored in a bone or a vertebra;
   a rod for connecting at least two anchoring elements, the rod having a longitudinal axis and being made of an elastic material;
   a receiving part being connected to the shank for receiving the rod;
   a seat for the rod being provided in the receiving part, the seat having a rod contacting surface;
   a locking device cooperating with the receiving part for fixation of the rod in the seat, the locking device comprising a rod contacting surface;
   wherein at least one of the rod contacting surface of the seat and the rod contacting surface of the locking device comprises an engagement structure extending transverse to the longitudinal axis when the rod is locked in the seat in the receiving part by the locking device; and
   wherein a cross section of the engagement structure in a plane containing the longitudinal axis of the seated rod comprises a first flank and a second flank opposite the first flank, wherein the first flank has a different inclination than the second flank with respect to a normal to the longitudinal axis to form an asymmetric cross section for the engagement structure.

2. The bone anchoring device according to claim 1, wherein the asymmetric cross section of the engagement structure is triangle-shaped.

3. The bone anchoring device according to claim 1, wherein the engagement structure is a rib-like projection.

4. The bone anchoring device according to claim 1, wherein the engagement structure comprises two rib-like projections spaced apart from a center of the rod contacting surface.

5. The bone anchoring device according to claim 1, wherein the rod is held in place by a frictional force exerted by the locking device with an indirect form-fit contribution with the engagement structure engaging the rod.

6. The bone anchoring device according to claim 1, wherein the receiving part is fixedly connected to the shank so as to provide a monoaxial bone anchoring device.

7. The bone anchoring device according to claim 6, wherein the receiving part has a U-shaped recess forming two open legs, and wherein the seat is provided at the bottom of the recess.

8. The bone anchoring device according to claim 1, wherein the receiving part is pivotably connected to the shank so as to provide a polyaxial bone anchoring device.

9. The bone anchoring device according to claim 8, wherein the seat is provided in a pressure element which is movable in the receiving part, and which locks the angular position of the bone anchoring element if pressure is exerted on the pressure element.

10. The bone anchoring device according to claim 1, wherein the locking device is a one-piece locking device which has the engagement structure at its lower side facing the rod.

11. The bone anchoring element according to claim 1, wherein the locking device is a two piece locking device comprising a set screw and a filling piece between the set screw and the rod, the engagement structure being provided at the lower side of the filling piece.

12. The bone anchoring device according to claim 1, wherein the rod is made of a free-flowing material.

13. The bone anchoring device according to claim 1, wherein the rod is made of an elastomeric material.

14. The bone anchoring device according to claim 1, wherein the engagement structure comprises a projection having two ends and a center between the two ends, and wherein a height of the projection varies over a length thereof.

15. The bone anchoring device according to claim 14, wherein the projection comprises a portion including the center and wherein the height in the portion decreases towards the center.

16. A bone anchoring device comprising:
   an anchoring element having a shank to be anchored in a bone or a vertebra;
   a rod for connecting at least two anchoring elements, the rod having a longitudinal axis and being made of an elastomeric material;
   a receiving part being connected to the shank for receiving the rod;
   a seat for the rod being provided in the receiving part, the seat having a rod contacting surface;
   a locking device cooperating with the receiving part for fixation of the rod in the seat, the locking device comprising a rod contacting surface; and
   wherein at least one of the rod contacting surface of the seat and the rod contacting surface of the locking device comprises an engagement structure for engaging the rod, the engagement structure comprising a first flank having a different inclination than a second flank with respect to a normal to the longitudinal axis of the rod to form an asymmetric cross section for the engagement structure.

17. A method of attaching a bone anchoring device to a bone or vertebrae, the bone anchoring device comprising an anchoring element having a shank to be anchored in a bone or a vertebra, a rod for connecting at least two anchoring elements, the rod having a longitudinal axis and being made of an elastic material, a receiving part being connected to the shank for receiving the rod, a seat for the rod being provided in the receiving part, the seat having a rod contacting surface, a locking device cooperating with the receiving part for fixation of the rod in the seat, the locking device comprising a rod contacting surface, wherein at least one of the rod contacting surface of the seat and the rod contacting surface of the locking device comprises an engagement structure extending transverse to the longitudinal axis when the rod is locked in the seat in the receiving part by the locking device, wherein a cross section of the engagement structure in a plane containing the longitudinal axis of the seated rod comprises a first flank and a second flank opposite the first flank, wherein the first flank has a different inclination than the second flank with respect to a normal to the longitudinal axis to form an asymmetric cross section for the engagement structure, the method comprising:

attaching the bone anchoring element to a bone or vertebrae;

connecting the rod to the receiving part;

securing the rod to the receiving part with the locking device; and wherein securing the rod with the locking device comprises the engagement structure engaging the rod to fix the rod to the receiving part.

* * * * *

UNITED STATES PATENT AND TRADEMARK OFFICE
CERTIFICATE OF CORRECTION

PATENT NO. : 8,277,494 B2
APPLICATION NO. : 12/175431
DATED : October 2, 2012
INVENTOR(S) : Lutz Biedermann et al.

It is certified that error appears in the above-identified patent and that said Letters Patent is hereby corrected as shown below:

In the Specification

| | |
|---|---|
| Column 2, line 3 | Delete "be" <br> Insert -- become -- |
| Column 2, line 4 | Delete "come" |
| Column 2, line 21 | After "of" <br> Insert -- the receiving part of the bone anchoring element of FIG. 4. -- |
| Column 2, line 22 | After "structure" <br> Delete "of the bone anchoring element of FIG. 5." |
| Column 3, line 27 | Delete "rib-likes" <br> Insert -- rib-like -- |

Signed and Sealed this
Sixth Day of May, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,277,494 B2 |
| APPLICATION NO. | : 12/175431 |
| DATED | : October 2, 2012 |
| INVENTOR(S) | : Lutz Biedermann et al. |

Page 1 of 1

It is certified that error appears in the above-identified patent and that said Letters Patent is hereby corrected as shown below:

In the Specification

Column 2, line 3                    Delete "be"
                                    Insert -- become --

Column 2, line 4                    Delete "come"

Column 2, line 21                   After "of"
                                    Insert -- the receiving part of the bone anchoring
                                    element of FIG. 4. --

Column 2, line 22                   After "structure"
                                    Delete "of the bone anchoring element of FIG. 5."

Column 3, line 26                   Delete "rib-likes"
                                    Insert -- rib-like --

This certificate supersedes the Certificate of Correction issued May 6, 2014.

Signed and Sealed this
Ninth Day of September, 2014

Michelle K. Lee
*Deputy Director of the United States Patent and Trademark Office*